(12) United States Patent
Lundgren et al.

(10) Patent No.: US 10,280,390 B2
(45) Date of Patent: May 7, 2019

(54) SYSTEM FOR CULTURE OF CELLS IN A CONTROLLED ENVIRONMENT

(71) Applicant: Saint-Gobain Performance Plastics Corporation, Aurora, OH (US)

(72) Inventors: Natasha Anna Lundgren, Boston, MA (US); Sarah Louise Clark, Somerville, MA (US); Edouard Civel, Paris (FR); Jeffrey Ellis Miripol, Hockessin (DE); Herbert Myers Cullis, Gaithersburg, MD (US); Phillippe Jean Broussard, Finksburg, MD (US)

(73) Assignee: Saint-Gobain Performance Plastics Corporation, Solon, OH (US)

( * ) Notice: Subject to any disclaimer, the term of this patent is extended or adjusted under 35 U.S.C. 154(b) by 539 days.

(21) Appl. No.: 14/976,091

(22) Filed: Dec. 21, 2015

(65) Prior Publication Data

US 2016/0177246 A1   Jun. 23, 2016

Related U.S. Application Data

(60) Provisional application No. 62/095,197, filed on Dec. 22, 2014.

(51) Int. Cl.
*C12M 1/04* (2006.01)
*C12M 1/00* (2006.01)
*C12M 1/12* (2006.01)

(52) U.S. Cl.
CPC ............ *C12M 23/24* (2013.01); *C12M 25/02* (2013.01); *C12M 29/04* (2013.01)

(58) Field of Classification Search
CPC ...... C12M 23/24; C12M 29/04; C12M 25/02; C12M 25/24; C12M 25/26; C12M 1/007; B01D 71/32
USPC .................................................. 210/321, 368
See application file for complete search history.

(56) References Cited

U.S. PATENT DOCUMENTS

| | | |
|---|---|---|
| 3,030,290 A | 4/1962 | Ryan et al. |
| 3,255,099 A | 6/1966 | Wolinski |
| 3,274,089 A | 9/1966 | Wolinski |
| 3,274,090 A | 9/1966 | Amborski |
| 3,274,091 A | 9/1966 | Amborski |
| 3,275,540 A | 9/1966 | McBride |
| 3,284,331 A | 11/1966 | McBride et al. |
| 3,291,712 A | 12/1966 | McBride |

(Continued)

FOREIGN PATENT DOCUMENTS

| | | |
|---|---|---|
| WO | 2006/119054 A2 | 11/2006 |
| WO | WO 2012031234 A2 | 3/2012 |

(Continued)

OTHER PUBLICATIONS

Copending U.S. Appl. No. 14/976,071, filed Dec. 21, 2015, corresponding to U.S. Patent Application Publication No. 2016/0178491.

(Continued)

*Primary Examiner* — Pamela H Weiss
(74) *Attorney, Agent, or Firm* — McDonnell Boehnen Hulbert & Berghoff LLP

(57) ABSTRACT

A cell culture container is provided, comprising membrane bound compartments for growing and harvesting monocytes that allows replenishing and removal of feed media without the loss or death of cells.

22 Claims, 6 Drawing Sheets

(56) References Cited

U.S. PATENT DOCUMENTS

| | | | |
|---|---|---|---|
| 3,296,011 A | 1/1967 | McBride et al. | |
| 3,391,314 A | 7/1968 | Carter | |
| 3,397,132 A | 8/1968 | Wolinski | |
| 3,485,734 A | 12/1969 | Pecka | |
| 3,507,763 A | 4/1970 | McBride | |
| 3,676,181 A | 7/1972 | Kowalewski | |
| 4,549,921 A | 10/1985 | Wolfe | |
| 4,829,002 A | 5/1989 | Pattillo et al. | |
| 4,847,462 A | 7/1989 | Soodak et al. | |
| 4,937,194 A | 6/1990 | Pattillo et al. | |
| 4,945,203 A | 7/1990 | Soodak et al. | |
| 5,225,346 A | 7/1993 | Matsumiya et al. | |
| 5,374,453 A * | 12/1994 | Swei | B29C 41/28 427/226 |
| 5,686,304 A | 11/1997 | Codner | |
| 5,935,847 A | 8/1999 | Smith et al. | |
| 6,060,317 A | 5/2000 | Malech | |
| 6,297,046 B1 | 10/2001 | Smith et al. | |
| 6,623,959 B2 | 9/2003 | Harris | |
| 6,638,728 B1 | 10/2003 | Desai et al. | |
| 6,726,979 B2 | 4/2004 | Friedman et al. | |
| 6,969,355 B2 | 11/2005 | Narimatsu | |
| 7,122,384 B2 | 10/2006 | Prober et al. | |
| 7,316,932 B2 | 1/2008 | Woodside | |
| 7,329,742 B2 | 2/2008 | Doyle et al. | |
| 7,514,075 B2 | 4/2009 | Hedrick et al. | |
| 8,138,289 B2 | 3/2012 | Kofinas et al. | |
| 8,318,438 B2 | 11/2012 | Vivekananda et al. | |
| 8,512,566 B2 | 8/2013 | Griffin et al. | |
| 8,727,132 B2 | 5/2014 | Miltenyi et al. | |
| 8,747,289 B2 | 6/2014 | Coelho | |
| 2003/0162190 A1 | 8/2003 | Gorenstein et al. | |
| 2006/0134606 A1 | 6/2006 | Montagu | |
| 2006/0199260 A1* | 9/2006 | Zhang | B01F 13/0059 435/293.1 |
| 2007/0042490 A1 | 2/2007 | Welter et al. | |
| 2008/0299649 A1 | 12/2008 | Martin et al. | |
| 2009/0239762 A1 | 9/2009 | Tan et al. | |
| 2009/0305389 A1 | 12/2009 | Willson et al. | |
| 2010/0304978 A1 | 12/2010 | Deng et al. | |
| 2012/0040395 A1 | 2/2012 | Clendennen | |
| 2012/0142088 A1 | 7/2012 | Hsiao et al. | |
| 2013/0040837 A1 | 2/2013 | Karp et al. | |
| 2013/0084622 A1* | 4/2013 | Ram | C12M 23/24 435/252.8 |
| 2013/0109086 A1 | 5/2013 | Kobayashi et al. | |
| 2013/0130361 A1 | 5/2013 | Okano et al. | |
| 2013/0236335 A1 | 9/2013 | Nelson et al. | |
| 2014/0066281 A1 | 3/2014 | Weasler et al. | |
| 2014/0148358 A1 | 5/2014 | Li et al. | |
| 2014/0255976 A1 | 9/2014 | Chang et al. | |
| 2016/0178490 A1 | 6/2016 | Civel et al. | |
| 2016/0178491 A1 | 6/2016 | Civel et al. | |

FOREIGN PATENT DOCUMENTS

| | | | |
|---|---|---|---|
| WO | WO 2012076190 A1 | 6/2012 | |
| WO | 2013048546 A1 | 4/2013 | |
| WO | WO 2013049860 A1 | 4/2013 | |
| WO | 2013/067399 A1 | 5/2013 | |
| WO | WO 2014120344 A2 | 8/2014 | |

OTHER PUBLICATIONS

International Preliminary Report on Patentability in International Patent Application No. PCT/US2015/067289, corresponding to U.S. Appl. No. 14/976,071, dated Jul. 6, 2017.
Copending U.S. Appl. No. 14/976,043, filed Dec. 21, 2015, corresponding to U.S. Patent Application Publication No. 2016/0178490.
International Preliminary Report on Patentability in International Patent Application No. PCT/US2015/067281, corresponding to U.S. Appl. No. 14/976,043, dated Jul. 6, 2017.
International Preliminary Report on Patentability in International Patent Application No. PCT/US2015/0672992, corresponding to U.S. Appl. No. 14/976,091, dated Jun. 27, 2017.
Albers, et al., "Structural and Functional Characteristics of Chimeric Avidins Physically Adsorbed onto Functionalized Polythiophene Thin Films." *ACS Applied Materials & Interfaces*, 2012, pp. 4067-4077.
Antharavally, et al., "Quantitation of Proteins using a Dye-metal-based Colorimetric Protein Assay." Analytical Biochemistry, No. 385, 2009, pp. 342-345.
Balamurugan, et al. "Surface immobilization methods for aptamer diagnostic applications" *Anal Bioanal Chem*, No. 390, 2008, pp. 1009-1021.
Coates, "Interpretation of Infrared Spectra, A Practical Approach." in Encyclopedia of Analytical Chemistry, Chichester: John Wiley & Sons, 2000, pp. 10815-10837.
Drumheller, et al., "Surface Immobilization of Adhesion Ligands for Investigation of Cell-Substreate Interactions", CRC Press LLC, 2003, pp. 9.1-9.14.
Fabre, et al., "Immobilization of Double Functionalized Carbon Nanotubes on Glassy Carbon Electrodes for the Electrochemical Sensing of the Biotin-avidin Affinity." *Journal of Electroanalytical Chemistry*, No. 665, 2012, pp. 90-94.
Gauvreau, et al. "Engineering Surfaces for Bioconjugation: Developing Strategies and Quantifying the Extent of the Reactions." *Bioconjugate Chem.*, 2004, pp. 1146-1156.
Heikkinen, et al., "Covalent Biofunctionalization of Cellulose Acetate with Thermostable Chimeric Avidin." *ACS Appl. Mater. Interfaces*, No. 3, 2011, pp. 2240-2245.
Lachmann, et al., "Surface modification of closed plastic bags for adherent cell cultivation." *Eur. Phys. J. Appl. Phys.*, No. 55, 2011, p. 13812.
McGettrick, et al., "A Substrate-Independent Approach for the Surface Immobilization of Oligonucleotides using Aldehyde Functionalized Surfaces." *Chem. Vap. Deposition*, No. 15, 2009, pp. 122-127.
Ocana, et al., "A Comparison of four protocols for the immobilization of an aptamer on graphite composite electrodes." Microchim Acta, No. 181, 2014, pp. 355-363.
Oh, et al., "Surface Modification for DNA and Protein Microarrays." *Journal of Integrative Biology*, vol. 10, No. 3, 2006, pp. 327-343.
Orelma, et al., "Generic Method for Attaching Biomolecules via Avidin-Biotin Complexes Immobilized on Films of Regenerated and Nanofibrillar Cellulose." *Biomacromolecules*, No. 13, 2012, pp. 2802-2810.
Ozer, et al., "New Technologies Provide Quantum Changes in the Scale, Speed, and Success of SELEX Methods nd Aptamer Characterization" *Molecular Therapy—Nucleic Acids*, No. 3, e183, 2014 pp. 1-18.
Ponche, et al., "Protein/Material Interfaces: Investigation on Model Surfaces." Journal of Adhesion Science and Technology, No. 24, 2010, pp. 2141-2164.
Rabe, et al,. "Understanding Protein Adsorption Phenomena at Solid Surfaces." *Advances in Colloid and Interface Science*, No. 162, 2011, pp. 87-106.
Racine, et al., "A Versatile Gradient of Biomolecules for Regulating Cell Behaviour." Journal of Adhesion Science and Technology, No. 24, 2010, pp. 975-992.
Srivastava, et al. "Polymer-antibody fragment conjugates for biomedical applications." *Progress in Polymer Science*, 2014, pp. 308-329.
Sromqvist, et al., "Binding of biotin to Streptavidin: A combined fluorescence correlation spectroscopy and time-resolved fluorescence study." *The European Physical Journal*, 2011, pp. 181-194.
Sun, et al., "Oligonucleotide Aptamers: New Tools for Targeted Cancer Therapy" *Molecular Therapy—Nucleic Acids*, 2014, pp. 1-14.
Tadahiro Ohmi, Ultra-Clean Technology Handbook: vol. 1: Ultra-Pure Water, CRC Press, 1993, pp. 497-517.
Tong, et al., "Peptide surface modification of poly(tetrafluoroethylene-co-hexafluoropropylene) enhances its interaction with central nervous system neurons." *Journal of Biomedical Materials Research*, 1998, pp. 85-95.

(56) References Cited

OTHER PUBLICATIONS

Vermette, et al., "Immobilization and Surface Characterization of Neutravidin Biotin-binding Protein on Different Hydrogel Interlayers." *Journal of Colloid and Interface Science*, No. 259, 2003, pp. 13-26.
Vesel, et al., "Adsorption of Protein Streptavidin to the Plasma Treated Surface of Polystyrene." *Applied Surface Science* 258, 2012, pp. 5558-5560.
Vesel, et al., "Immobilization of Protein Streptavidin to the Surface of PMMA Polymer." *Vacuum*, No. 86, 2012, pp. 773-775.
Xia, et al., "Ultra Sensitive Affinity Chromatography on Avidin-functionalized PMMA Microchip for Low Abundant Post-translational Modified Protein Enrichment." *Biomedical Microdevices*, 2012 pp. 67-81.
Ye, et al., "Generating Aptamers by Cell-SELEX for Applications in Molecular Medicine" *Int. J. Mol. Sci.*, No. 13, 2012, pp. 3341-3353.
Yun, et al., "Human monocyte/macrophage adhesion and cytokine production on surface-modified poly(tetrafluoroethylene/hexafluoropropylene) polymers with and without protein preadsorption." *Journal of Biomedical Materials Research*, vol. 29, 1995, pp. 257-268.
Zhou, et al., "Cell-type-specific, Aptamer-functionalized Agents for Targeted Disease Therapy" *Molecular Therapy—Nucleic Acids*, 2014, pp. 1-17.

\* cited by examiner

SYSTEM FOR CULTURE OF CELLS IN A CONTROLLED ENVIRONMENT

CROSS REFERENCE TO RELATED APPLICATIONS

This application claims benefit under 35 U.S.C. § 119(e) to U.S. Ser. No. 62/095,197, entitled "SYSTEM FOR CULTURE OF CELLS IN A CONTROLLED ENVIRONMENT", filed Dec. 22, 2014, the contents of which is incorporated herein by reference in their entirety.

FIELD OF THE INVENTION

The invention relates generally to a cell culture apparatus and a cell culture method.

BACKGROUND OF THE INVENTION

In vitro cell culture is the complex process by which cells are grown under controlled conditions, generally outside of their natural environment but as close to their natural in vivo conditions as possible. In practice cell culture refers to the culturing of cells derived from multi-cellular eukaryotes, especially animal cells. However, there are also cultures of plants, fungi, insects and microbes, including viruses, bacteria and protista.

In vitro cell culture provides material necessary for research and application in pharmacology, physiology, and toxicology. This includes bioprocessing and cell therapy where cell cultures are necessary.

Cells are grown and maintained at an appropriate temperature and gas mixture in a cell incubator. Typically, mammalian cells are incubated at 37° C. with a pH maintained between 7.2 and 7.4. The pH is typically controlled using a bicarbonate buffering system in the medium, in conjunction with an incubator atmosphere of approximately 5-7% carbon dioxide by volume. The carbon dioxide reacts with the water to form carbonic acid which in turn interacts with bicarbonate ions in the medium to form a buffering system which maintains the pH near physiological levels. Oxygen is essential for cellular metabolism and growth. Culture conditions can vary for each cell type, and variation of conditions for a particular cell type can result in different phenotypes. For instance, bicarbonate based buffers can be substituted with mono and di or tri-sodium phosphate buffers, chloride and ammonia buffers, lactate, or organic buffers such as HEPES, etc.

A variety of cell types are grown in vitro and similarly a variety of media are available depending on the particular growth requirements of the cells and the growth conditions.

Monocytes are the largest type of white blood cells (leukocytes) and are an important part of the innate immune system of vertebrates including all mammals. Monocytes are the circulating precursors of macrophages and dendritic cells that migrate from the blood stream across vascular endothelium for immunological surveillance and inflammation response.

Commercially available gas permeable cell culture devices in the form of bags are currently a standard device format used for cell culture. Cell culture bags have the advantage of being disposable, which reduces preparation and clean up time. Additionally, cell culture bags are pre-sterilizable, inexpensive, easy to use and require minimal space for storage and use. Disposables also helps reduce the risk of contamination for the cell culture and for the environment.

Gas permeable cell culture bags are commercially available from OriGen Biomedical Group (OriGen PermaLife™ Bags), Baxter (Lifecell® X-Fold™ related to U.S. Pat. Nos. 4,829,002, 4,937,194, 5,935,847, 6,297,046 B1), Medtronic (Si-Culture™, U.S. Pat. No. 5,686,304), Biovectra (Vectra-Cell™), and American Fluoroseal (VueLife™ Culture Bag System, covered by U.S. Pat. Nos. 4,847,462 and 4,945,203).

For example, one problem of conventional fluoropolymer cell culture bags is that the feed media and cells are mixed within the culture chamber and therefore the amount of media added is limited to the volume of the container. In one example, Matsumiya et al. (U.S. Pat. No. 5,225,346) attempts to correct the problem of media supply by integrating the bag with a medium storage compartment. The culture chamber and medium storage compartment are connected and when fresh medium is needed it is passed from the medium storage compartment to the culture chamber.

Another problem of conventional fluoropolymer cell culture bags is removal of media having diminished nutrient content and increased waste content during cell cultivation which may unavailingly remove cells as well. Additionally, manual manipulation of the culture is generally necessitated to replenish the medium.

Perfusion is a continuous process in which adherent or suspension cell culture is continuously supplied with fresh medium to the bioreactor while spent culture media is continuously harvested. For the latter, cells are continuously filtered from the harvest stream and returned to the bioreactor to maintain a constant culture volume. This continuous process allows the cells to reach high densities as densities of 10-15 million cells/mL can routinely be reached and maintained for extended periods of time. This process is limited to complex perfusion bioreactors that require large volumes of media. In the present embodiments, it is preferred that the cell culture medium above the cell containing compartment is perfused such that the cells are not appreciably moved about.

Therefore, a need exists for a simplified perfusion apparatus that allows removal and replenishment of feed media without diminishing cell count thereby advantageously concentrating cells over a period of time not controlled by feed media supply limitations.

BRIEF SUMMARY OF THE INVENTION

An apparatus and method for cell cultivation that overcomes one or more of the disadvantages known in the art is provided. It has been discovered that it is possible to prepare a perfusion cell culture container comprising membrane bound compartments for growing and harvesting cells that allows replenishing and removal of feed media without the loss and/or death of cells.

In a first embodiment, a container comprising a gas permeable outer film comprising a polymer having a total organic carbon (TOC) in water of less than 0.1 mg/cm$^2$, a membrane separating a first compartment from a second compartment, wherein the membrane comprises a polymer having a TOC in water of less than 0.1 mg/cm$^2$, and wherein the gas permeable outer film and the membrane define walls of the first and second compartments is presented.

In a second embodiment, a container comprising a gas permeable outer film comprising a polymer having a total organic carbon (TOC) in water of less than 0.1 mg/cm$^2$, a first membrane separating a central compartment from a first lateral compartment, and a second membrane separating the central compartment from a second lateral compartment, wherein the central compartment is between the first and second lateral compartments, wherein the first and second membranes both comprise a polymer having a TOC in water of less than 0.1 mg/cm$^2$, and wherein the gas permeable outer film and the first and second membranes define walls of the first lateral, second lateral, and central compartments is presented.

In one aspect, the outer film and the membrane or membranes of the container are each individually an elastomer, a fluoropolymer, PMP (polymethylpentene), or combinations thereof. In another aspect the gas permeable outer film is a silicone and the membrane or membranes are a fluoropolymer.

In an another embodiment the membranes can include fluoropolymers that are each individually FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), PCTFE (polychlorotrifluoroethylene), ETFE (polyethylenetetrafluoroethylene), ECTFE (polyethylenechlorotrifluoroethylene), FFPM/FFKM (perfluoroelastomer), FPM/FKM (chlorotrifluoroethylenevinylidene fluoride), PFPE (perfluoropolyether), MFA (tetrafuoroethylene and perfuoromethyl vinyl-ether copolymer), CTFE/VDF (chlorotrifuoroethylene-vinylidene fluoride copolymer), and TFE/HFP (tetrafuoroethylene-hexafuoropropylene copolymer), or mixtures thereof.

In another embodiment the fluoropolymer membranes comprises holes formed by laser drilling such as UV-IR, picosecond, femtosecond, excimer and CO$_2$ laser drilling, electron beam drilling, electrical discharge machining, mechanical drilling, or thermal perforation.

In one aspect the holes of the membrane are up to 5 mm in diameter.

In another aspect the holes of the membrane are greater than 100 microns, greater than 500 microns, and up to 5 mm in diameter.

In another aspect the holes of the membrane are from about 50 to about 100 microns in diameter.

In another aspect the porosity of the membrane is from about 10% to about 90%.

In another aspect the porosity of the membrane is from about 20% to about 70%.

In still another aspect the porosity of the membrane from about 30% to about 50%.

In another embodiment the fluoropolymer membranes are attached to the container by RF welding, ultrasonic welding, hot bar welding, laser welding, chemical bonding, adhesive bonding, thermal fusion bonding, solvent bonding, welding, surface treatment, or combinations thereof.

In another embodiment the container comprises at least two ports, wherein a first port is attached to the first compartment, a second port is attached to the second compartment.

In another embodiment the container comprises at least three ports, wherein a first port is attached to the first lateral compartment, a second port is attached to the second lateral compartment, and a third port is attached to the central compartment.

In still another embodiment the ports comprise an elastomer, a fluoropolymer, PMP (polymethylpentene), or combinations thereof.

In yet another embodiment the ports are attached to the container by collar sealing, such as by RF welding, ultrasonic welding, hot bar welding, laser welding, chemical bonding, adhesive bonding, thermal fusion bonding, solvent bonding, welding, surface treatment, or combinations thereof.

In another embodiment a method is disclosed to cultivate cells in a container comprising a gas permeable outer film comprising a polymer having a total organic carbon (TOC) in water of less than 0.1 mg/cm$^2$; a membrane separating a first compartment from a second compartment, wherein the membrane comprises a polymer having a TOC in water of less than 0.1 mg/cm$^2$, and wherein the gas permeable outer film and the membrane define walls of the first and second compartments. The method comprises the steps of a) adding cells and medium to the first compartment through the first port; b) adding media to the second compartment through the second port; and c) removing waste media from the second compartment through the second port or a third port, wherein media nutrients, metabolites, and cell culture additives permeate from between the first and second compartment through the membrane.

In another embodiment a method is disclosed to cultivate cells in a container comprising a gas permeable outer film comprising a polymer having a total organic carbon (TOC) in water of less than 0.1 mg/cm$^2$; a first membrane separating a central compartment from a first lateral compartment; and a second membrane separating the central compartment from a second lateral compartment, wherein the central compartment is between the first and second lateral compartments, wherein the first and second membranes both comprise a polymer having a TOC in water of less than 0.1 mg/cm$^2$, and wherein the gas permeable outer film and the first and second membranes define walls of the first lateral, second lateral, and central compartments. The container also includes at least three ports, wherein the first port is attached to the first lateral compartment, the second port is attached to the second lateral compartment, and the third port is attached to the central compartment. The method comprises the steps of a) adding cells to the central compartment through the third port; b) adding media to the first lateral compartment through the first port; and c) removing waste media from the second lateral compartment through the second port, wherein the media permeates from the first lateral compartment to the central compartment through the first fluoropolymer membrane and the waste media permeates from the central compartment to second lateral compartment through the second fluoropolymer membrane.

In another embodiment the outer film of the containers used in the methods is silicone TPU or an elastomer, a fluoropolymer, PMP (polymethylpentene), or combinations thereof. The membranes in the methods can be made of fluoropolymers.

In another embodiment of the method the container is incubated.

In another embodiment the cell incubation is static.

In still another embodiment the media flows through the container.

In yet another embodiment the cells are harvested from their respective compartment through the attached port.

In another embodiment the diameter of the holes of the membrane are sufficient to retain the cells within their respective compartment.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention.

Accordingly, the detailed descriptions are to be regarded as illustrative in nature and not restrictive.

BRIEF DESCRIPTION OF THE DRAWINGS

These and other features and advantages of the various embodiments disclosed herein will be better understood with respect to the following description and drawings, in which like numbers refer to like parts throughout.

DETAILED DESCRIPTION

In the specification and in the claims, the terms "including" and "comprising" are open-ended terms and should be interpreted to mean "including, but not limited to . . . " These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The current disclosure allows for the removal and replenishment of feed media from a cell culture apparatus without diminishing cell count thereby advantageously concentrating cells over a period of time not controlled by feed media supply limitations.

The culture container disclosed comprises an outer film with at least two ports that allow access to the interior compartments of the container. Oxygen is necessary for cellular growth in a medium and carbon dioxide is necessary for a medium to buffer pH. A pH range of 7.4-7.6 is optimal for normal cell growth and pH that fall outside of this range, for example, a pH higher than 7.8 can inhibit normal cell growth. Therefore it is necessary for the culture bag to have a good supply of both oxygen and carbon dioxide.

Those skilled in the art will recognize that the outer film of the cell culture container should be selected based on a variety of characteristics including gas permeability, flexibility, heat-sealability that ensures airtightness, good clarity that permits the microscopic examination of cell growth, freedom from plasticizers (such as dioctyl phthalate and diisodecyl phthalate) that can be harmful to cells, moisture vapor transmission, capacity to be altered for desired cell interaction with cells, optical clarity, physical strength, and the like.

Figure 1:
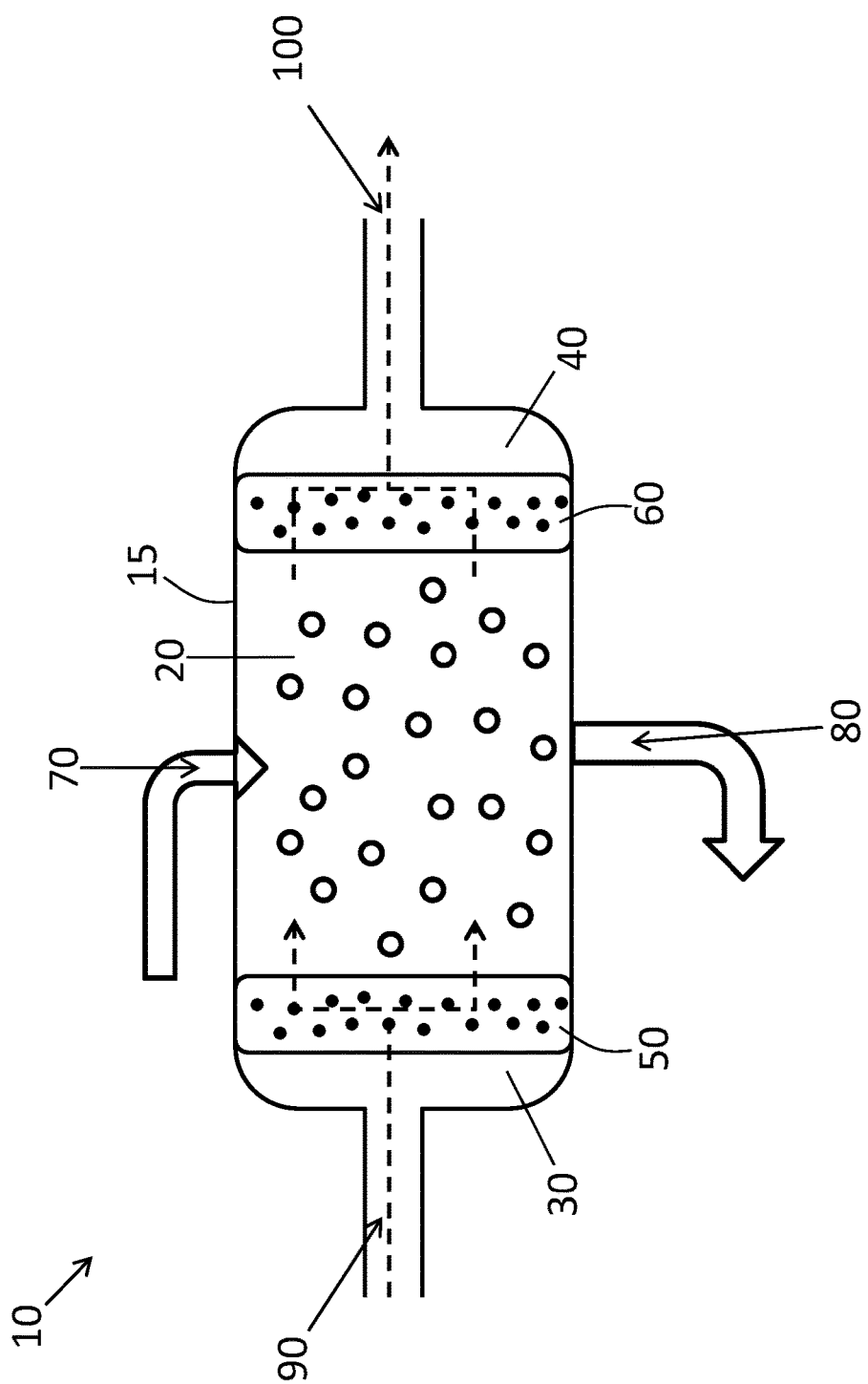
FIG. 1 shows a cross-section view of the three compartment cell culture container described herein.

FIG. 1 shows a cross-sectional view of a three compartment cell culture container 10 described herein. Container 10 comprises gas permeable outer film 15, first internal fluoropolymer membrane 50, and second internal fluoropolymer membrane 60. Outer film 15 and attached internal membranes 50 and 60 give rise to central compartment 20, first lateral compartment 30, and second lateral compartment 40. Membranes 50 and 60 are semi-permeable that act as barriers to cells within central compartment 20. It is without limitation that membrane placement can be in the x direction (i.e. cutting the bag in half horizontally) as well as in the y direction (i.e. cutting the bag in half vertically) as well as in the z direction (i.e. cutting the bag in half towards the plane).

Figure 2:
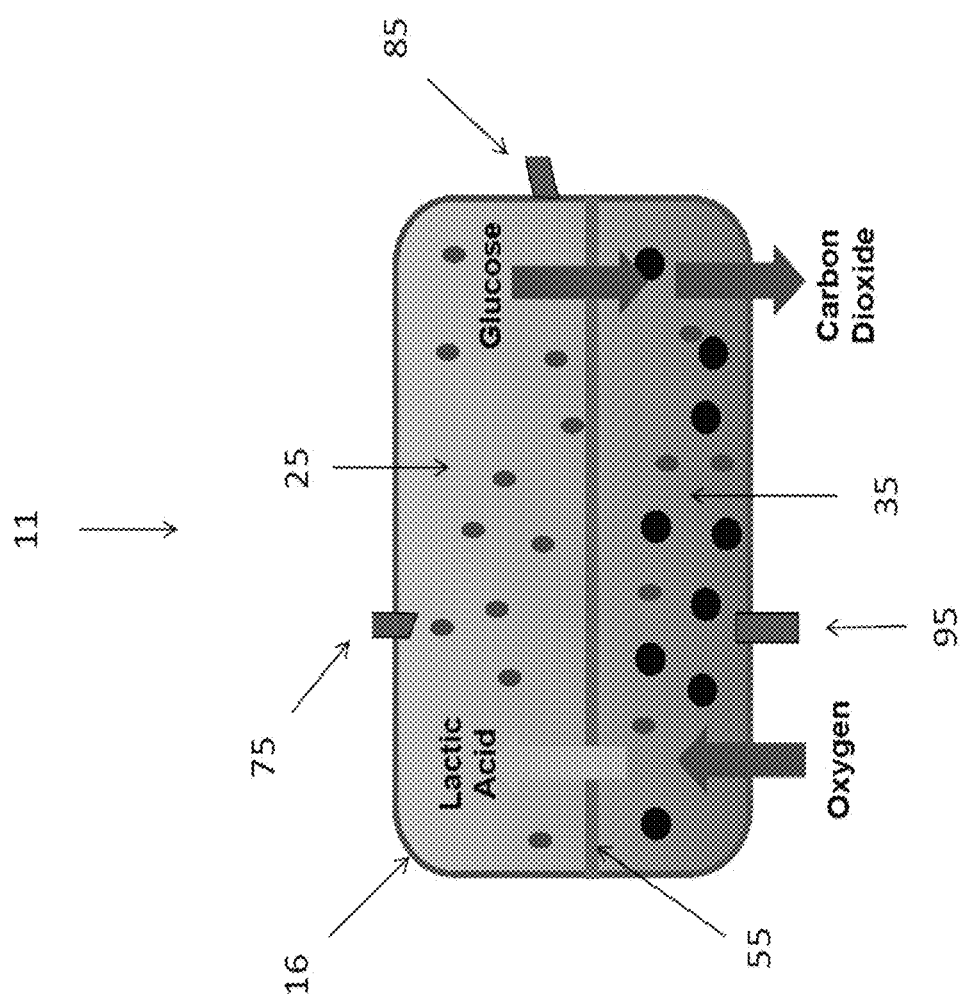
FIG. 2 shows a cross-section view of a two compartment cell culture container.

FIG. 2 show a cross-sectional view of a two compartment cell culture container 11. Container 11 comprises gas permeable outer film 16, internal fluoropolymer membrane 55 that gives rise to first compartment 25 and second compartment 35. Membrane 55 is semi-permeable that acts as a barrier to the cells within the second compartment 35.

Containers 10 and 11 are not limited to having consistent gas permeability throughout the entire gas permeable outer films 15 and 16. Some areas or parts of the containers may be more gas permeable than other areas or parts. For example, the cell cultivation compartment or second compartment 35 of container 11 can be more gas permeable than first compartment 25. In another aspect the more gas permeable part can include either the whole bottom or a portion of the bottom of the cell cultivation compartment or second compartment 35 of container 11. In yet another aspect, a perforated tube can be used inside the cell compartment to allow for uniform flow across the width of the bag.

Container 10 comprises gas permeable outer film 15 and container 11 comprises gas permeable outer film 16 constructed from at least two sheets of film that are bonded together at their edges to form a sealed bag. The containers may be prepared by bonding several sheets of material together. For instance three sheets of material comprising an outer film, an inner membrane, and an outer film may be layered and bonded together at once. The method of bonding can be by coating, RF welding, ultrasonic welding, hot bar welding, chemical bonding, adhesive bonding, thermal fusion bonding, solvent welding, laser welding, corona discharge, radiation, surface treatment, extreme heat, belt, or melt lamination, etching, plasma treatment, extrusion, wetting, adhesives, or combinations thereof. Preferred methods of welding include thermal, laser, and hot bar welding.

Preferred methods of surface treatment include C-treatment (Saint-Gobain Performance Plastics Corporation, U.S. Pat. No. 6,726,979), corona discharge, plasma treatment, etching, or combinations thereof. Surface treatments may also involve chemical treatment with additives or primers that can be used alone or in conjunction with the other disclosed treatment methods.

The layers may also be prelaminated together similar to that described for LIGHTSWITCH® Complete product (Saint-Gobain Performance Plastics Corporation, Valley Forge, Pa.).

Gas permeable outer film 15 of container 10 and gas permeable outer film 16 of container 11 can be an elastomer, a fluoropolymer, PMP (polymethylpentene), or combinations thereof.

The elastomer of gas permeable outer films 15 and 16 can be natural polyisopene rubber (NR), synthetic polyisoprene rubber (IR), polybutadiene rubber (BR), chloropene rubber (CR), butyl rubber (IIR), halogenated butyl rubbers (CIIR, BIIR), styrene-butadiene rubber (SBR), nitrile rubber (NBR) and hydrogenated nitrile rubber (HNBR), ethylene propylene rubber (EPM), ethylene propylene diene rubber (EPDM), epichlorohydrin rubber (ECO), polyacrylic rubber (ACM, ABR), silicone rubber (SI, Q, VMQ), fluorosilicone rubber (FSR, FVMQ), fluoroelastomers (FKM, FEPM), perfluoroelastomers (FFKM), polyether block amides (PEBA), chlorosulfonated polyethylene (CSM), ethylene-vinyl acetate (EVA), cyclic olefin copolymers, polyolefin elastomers, elastomeric PET, or mixtures thereof.

Elastomers are polymers with viscoelastic properties, low crystallinity, and high amorphous content, generally having low Young's modulus and high elongation at break compared to other materials. The term elastomers may be used interchangeably with the term rubber, although rubber is preferred when referring to vulcanisates. Elastomers are amorphous polymers constructed from monomers of carbon, hydrogen, oxygen, and/or silicon.

Thermoplastic polyurethanes (TPUs) are known in the art. Typically, a thermoplastic polyurethane is formed by reacting a polyol with an isocyanate. The overall properties of the polyurethane will depend upon the type of polyol and isocyanate, crystallinity in the polyurethane, the molecular weight of the polyurethane and chemical structure of the polyurethane backbone.

Polyurethanes may be either thermoplastic or thermoset, depending on the degree of crosslinking present. Thermoplastic urethanes (TPUs) do not have primary crosslinking while thermoset polyurethanes have a varying degree of crosslinking, depending on the functionality of the reactants.

Thermoplastic polyurethanes are commonly based on either methylene diisocyanate (MDI) or toluene diisocyanate (TDI) and include both polyester and polyether grades of polyols. Thermoplastic polyurethanes can be formed by a "one-shot" reaction between isocyanate and polyol or by a "pre-polymer" system, wherein a curative is added to the partially reacted polyolisocyanate complex to complete the polyurethane reaction. Examples of some common thermoplastic polyurethane elastomers based on "pre-polymers" are "TEXIN", a tradename of Bayer Materials Science, "ESTANE", a tradename of Lubrizol, "PELLETHANE", a tradename of Dow Chemical Co., and "ELASTOLLAN", a tradename of BASF, Inc.

GENIOMER® thermoplastic silicones include, but are not limited to GENIOMER® 140 Silicone TPE, GENIOMER® 200 Silicone TPE Elastomer (90% polydimethylsiloxane and isocyanate), GENIOMER®, 60 Silicone TPE, GENIOMER® 80 Silicone TPE and GENIOMER® 145 TPE, all of which comprise 90% polydimethylsiloxane and isocyanate.

It should also be noted that other configurations of thermoplastics (elastomer and non-elastomer) and fluoropolymer configurations could also be used to control the gas permeability of a composite, whilst containing a low TOC fluid contact layer. Control of gas permeability could be for purpose of either creating a high or low gas permeable composite. Examples of thermoplastics elastomers (TPE) include styrene block copolymers (TPE-s), olefins (TPE-o), alloys (TPE-v or TPV), polyurethanes (TPU), copolyesters, and polyamides. Examples of non-elastomer thermoplastics include acrylics, acrylonitrile butadiene styrene (ABS), nylon, polylactic acid (PLA), polybenzimidazole (PBI), polycarbonate (PC), polyether sulfone (PES), polyetherether ketone (PEEK), polyetherimide (PEI), polyethylene (PE), polyphenylene oxide (PPO), polyphenylene sulfide (PPS), polypropylene (PP), polystyrene (PS), and polyvinyl chloride (PVC), ethylene vinyl alcohol (EVOH), as well as any traditionally rigid polymer whose monomer architecture has been modified to reduce crystallinity and increase flexibility.

The fluoropolymer of gas permeable outer films 15 and 16 can be FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), 3M™ Dyneon™ TFM™ modified PTFE, PCTFE (polychlorotrifluoroethylene), HTE (tetrafluoroethylene/hexafluoropropylene/ethylene copolymer), ETFE (polyethylenetetrafluoroethylene), ECTFE (polyethylenechlorotrifluoroethylene), FFPM/FFKM (perfluoroelastomer), FPM/FKM (chlorotrifluoroethylene/vinylidene fluoride copolymer), PFPE (perfluoropolyether), MFA (tetrafuoroethylene and perfuoromethyl vinyl-ether copolymer), CTFE/VDF (chlorotrifuoroethylene-vinylidene fluoride copolymer), TFE/HFP (tetrafuoroethylene-hexafuoropropylene copolymer), chlorotrifluoroethylene/hexafluoropropylene, THV (hexafluoropropylene/tetrafluoroethylene/vinylidene copolymer), perfluoro(1-butenyl vinyl ether)homocyclopolymer having functionalized polymer-end groups, or mixtures thereof.

The PMP (polymethylpentene) of the gas permeable outer films 15 and 16 is a thermoplastic polymer of methylpentene monomer units. It has been used for gas permeable packaging, autoclavable medical and laboratory equipment, microwave components, and cookware. It is commercially available as TPX™ from Mitsui Chemicals America, Inc, Rye Brook, N.Y.

In one embodiment a cell culture container may comprise a single layer of an elastomer, such as a thermoplastic silicone (e.g. GENIOMER® by Wacker Chemie AG, a polydimethylsiloxane/urea copolymer) or a fluoropolymer with TOC and permeability properties as described herein.

The gas permeable outer films 15 and 16 may also comprise a laminate including the above mention materials.

Figure 3:
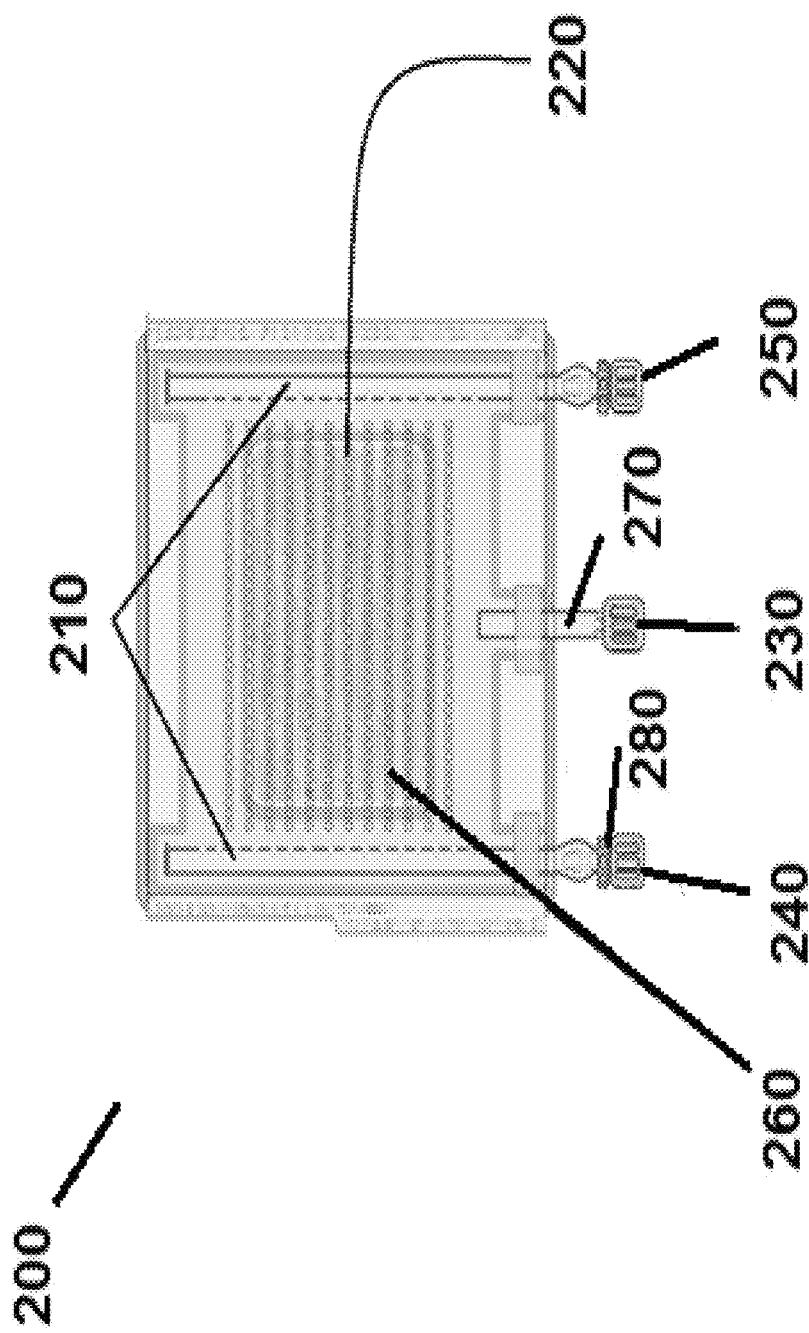
FIG. 3 shows a top view of a membrane bag where the gas permeable laminate is a portion of the bottom of the bag.
Figure 4:
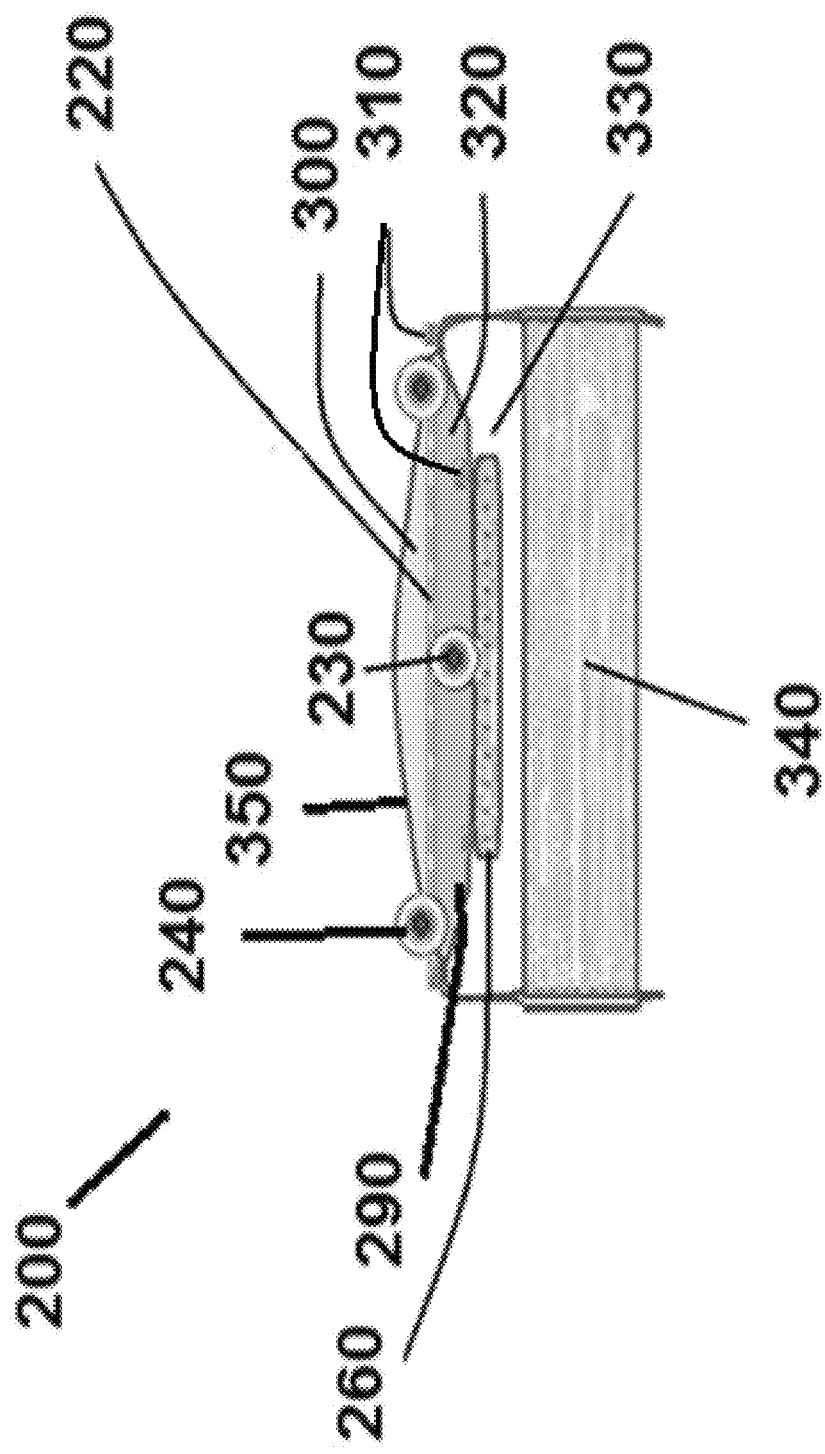
FIG. 4 shows a side view of the membrane bag of FIG. 3 also showing a support stand.
Figure 5:
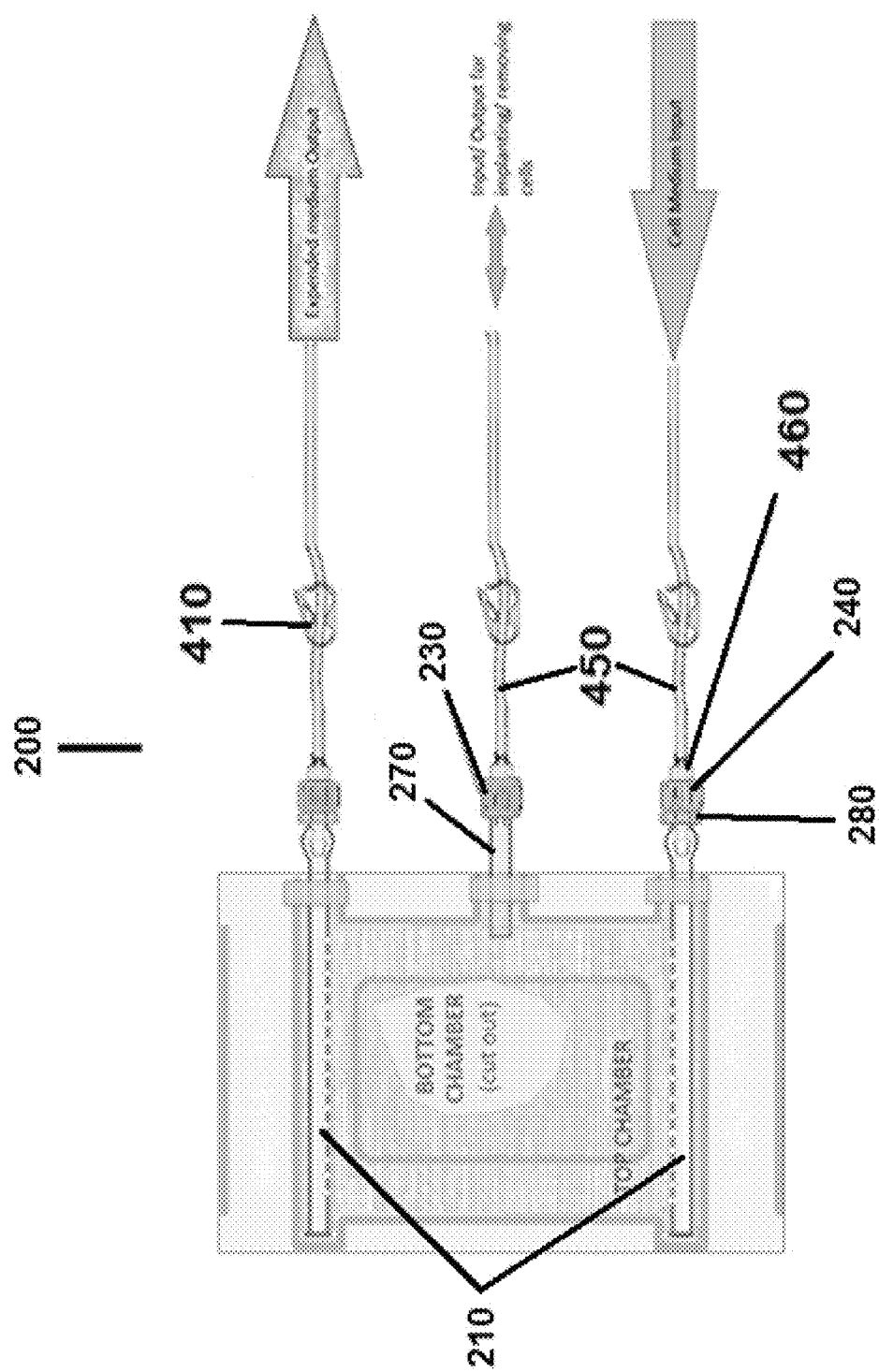
FIG. 5 shows a membrane bag in another embodiment of the current invention.

FIGS. 3, 4, and 5 show an example of a membrane bag 200 where gas permeable laminate is not the complete bottom of the membrane bag but instead a portion of the bottom of the membrane bag. Membrane bag 200 may also have frame 340 that allows the bag to be lifted off a solid surface. Membrane bag 200 is shown having perforated tubes 210 with upper chamber access ports 240 and 250 and perforated "bulk-head" perfusion layer 220 overtop of FEP/silicone laminate 260. In a particular aspect 260 is 1 mil FEP/7 mil silicone laminate. In one example, 240 and 250 also point to the male end of a Leur barbed connector, 280 refers to the female end of a Leur barbed connector, and 270 can be a standard FEP ¼ inch Leur port. Bottom chamber is accessed through bottom chamber access port 230. FIG. 4 more clearly shows upper chamber 300, laser welded seams 310, bottom chamber 320, and space between membrane bag 200 and frame 340. Frame 340 can be a 30 mil FEP stand-off support frame. FIG. 5 shows membrane bag 200 connected to connection tubes 450 for expended medium output, input/output for implanting/removing cells, and cell medium input. FIG. 5 also shows tube clamp (x3) 410 and retaining ring (x3) 460. Retaining ring can be an FEP retaining ring if tube is standard 4 mm PVC tubing.

Total Organic Carbon (TOC) is the amount of carbon bound in an organic compound and is often used as a non-specific indicator of pharmaceutical manufacturing equipment, among other things. TOC is utilized as a process control attribute in the biotechnology industry to monitor the performance of unit operations that employ purification and distribution systems.

In specific embodiments, TOC may be measured according to US Pharmacopeia (USP) 643 and with equipment that utilizes a high temperature wet oxidation reaction of UV-promoted chemical oxidation (*Ultra-Clean Technology Handbook: Volume* 1: *Ultra-Pure Water*, Ohmi, Tadahiro; CRC Press, 1993, pp. 497-517). Purified water is placed in contact with the polymer for 24 hours at 70° C., for example at a ratio of 3 cm$^2$ of article surface area to 1 mL of water. The water is removed from contact with the polymer and tested in a TOC analyzer. A suitable piece of equipment is a TEKMAR DOHRMANN Model Phoenix 8000 TOC analyzer.

In particular embodiments, TOC may be measured for a container employed in a system of the disclosure including, for example by extraction from an internal surface area of the container (with results reflected as mg/cm$^2$ are for the TOC per square centimeter of the internal area). In specific embodiments, and merely as an example, the container may be extracted in purified water 70±2° C. for 24±2 hours. The extract may be analyzed for TOC by converting TOC to carbon dioxide by acidification and chemical wet oxidation with sodium persulfate, for example. The carbon dioxide liberated from the container may be measured using an infrared detector. An example of an extraction ratio for a FEP container is 3 cm$^2$/mL (a typical extraction ratio). For some containers (such as FEP bags), no dilution is required because the level of TOC is less than the upper limit of a calibration curve, whereas for other embodiments (such as silicone tubing), dilution is required because of the levels of the TOC detected in the extract.

An example of TOC for a FEP container is 0.145 mg/L (0.00 mg/cm$^2$ or 0.001 mg/g). For embodiments that employ silicone tubing, extraction ratios may be 14.6 cm$^2$/mL (such as for Biosil), or may be 15.9 cm$^2$/mL (such as for SR139), and an example of TOC for silicone Biosil tube is 302 mg/L (0.021 mg/cm$^2$ or 0.023 mg/cm), and an example of TOC for silicone SR139 tubing is 120 mg/L (0.008 mg/cm$^2$ or 0.0009 mg/cm). In at least certain silicone tubing embodiments, the samples may be diluted, as the volume and concentration of the extraction cause the value to be above the maximum detection of the machine. The dilution and different extraction ratio requires the comparison of these samples with the bag samples to be made on the weight/area value basis instead One of skill in the art recognizes that TOC values may be characterized in weight/volume. However, persons of skill in the art acknowledge that ratios for the container (particularly a FEP bag material) vs. ratios for silicone tubing are distinguishable; silicone tubing values can only be considered on a mg/cm$^2$ starting basis, as this value is independent of extraction ratio/dilution. One of skill in the art can calculate a "normalized" weight/volume ratio using a weight/area result as a basis and assuming a standard 3 cm$^2$/mL extraction ratio (as an example) in order to compare values on a weight/volume value.

In specific embodiments, the TOC of thermoplastic elastomers (TPE) is 0.002 mg/cm$^2$ (0.032 mg/g or 5.88 mg/mL).

In certain embodiments, the TOC of FEP is 0.00005 mg/cm$^2$ (0.001 mg/g or 0.145 mg/mL). In specific embodiments, the TOC of silicone is 0.021 mg/cm$^2$ or 63 mg/mL of interior wetted surface of an article. In a specific embodiment, a TOC for a PMP film is 0.07 ppm (0.00001 mg/cm$^2$).

In specific embodiments, the TOC of fluorinated ethylene propylene (FEP) is 0.00005 mg/cm$^2$ of interior wetted surface of an article (0.001 mg/g or 0.145 mg/g of article); the TOC of silicone materials, such as silicone tubing of interior wetted surface of an article, is 0.021 mg/cm$^2$ or 63 mg/mL (0.023 mg/cm) and 0.008 mg/cm$^2$ (0.009 mg/cm) of interior wetted surface of an article; the TOC for a historically used cell culture bag is 0.002 mg/cm$^2$ of interior wetted surface of an article (0.032 mg/g or article).

One of skill in the art recognizes that TOC values may be compared across different extraction ratios/dilutions if mg/cm$^2$ units are employed. If units are mg/L, an extraction ratio must be known. A conversion may occur as follows: the machine outputs a value in mg/L, dilution is factored in, and then this number is converted to mg/cm$^2$ using the surface area and total volume to extract. An example for Silicone Biosil is provided: Silicone Biosil Sample: 302 mg/L*1 L/1000 mL*23.7 mL/347 cm$^2$=0.021 mg/cm$^2$.

In a particular embodiments, TOC is compared in mg/cm$^2$ units because the extraction ratio or any dilution is not needed. Below is an example of TOC calculation on a Silicone Tube Biosil sample and on Silicone Tube SR139 sample.

Test Article Extraction

| Sample | Internal Surface Area (cm$^2$) | Length (cm) | Volume of Purified Water (mL) |
|---|---|---|---|
| Silicone Tube Biosil Sample | 347 | 314 | 23.7 |
| Silicone Tube SR139 Sample | 342 | 295 | 21.5 |

Results for TOC Analysis

| Sample | mg/L | mg/cm$^2$ | mg/cm | Detection Limit (mg/L) |
|---|---|---|---|---|
| Silicone Tube Biosil Sample | 302 | 0.021 | 0.023 | 0.1 |
| Silicone Tube SR139 Sample | 120 | 0.008 | 0.009 | 0.1 |

Below is an example of TOC calculation on a FEP Bag and on a single layer bag mostly composed of a SEBS (styrene block copolymer) but also may contain EVA and PP:

Test Article Extraction

| Sample | Internal Surface Area (cm$^2$) | Weight (g) | Volume of Purified Water (mL) |
|---|---|---|---|
| FEP Bag | 650 | 30.9 | 217 |
| SEBS Bag | 362.9 | 22.5 | 121 |

Results for TOC Analysis

| Sample | mg/L | mg/cm² | mg/g | Detection Limit (mg/L) |
|---|---|---|---|---|
| FEP Bag | 0.145 | 0.00 | 0.001 | 0.1 |
| SEBS Bag | 5.88 | 0.002 | 0.032 | 0.1 |

In specific embodiments, a container comprises an inner surface comprising a polymer having a total organic carbon (TOC) in water of less than 1 mg/cm², 0.9 mg/cm2, 0.8 mg/cm², 0.7 mg/cm², 0.6 mg/cm², 0.5 mg/cm², 0.4 mg/cm², 0.3 mg/cm², 0.2 mg/cm², 0.1 mg/cm², 0.09 mg/cm², 0.08 mg/cm², 0.07 mg/cm², 0.06 mg/cm², 0.05 mg/cm², 0.04 mg/cm², 0.03 mg/cm², 0.02 mg/cm², 0.01 mg/cm², 0.009 mg/cm², 0.008 mg/cm², 0.007 mg/cm², 0.006 mg/cm², 0.005 mg/cm², 0.004 mg/cm², 0.003 mg/cm², 0.002 mg/cm², 0.001 mg/cm², and so forth.

In particular embodiments, the TOC in water is less than an amount in a range from 0.001 mg/cm² to 0.1 mg/cm², 0.001 mg/cm² to 0.095 mg/cm², 0.001 mg/cm² to 0.075 mg/cm², 0.001 mg/cm² to 0.05 mg/cm2, 0.001 mg/cm² to 0.01 mg/cm2, 0.001 mg/cm² to 0.005 mg/cm², or 0.001 mg/cm² to 0.025 mg/cm². In particular embodiments, the TOC in water is less than an amount in a range from 0.01 mg/cm² to 0.1 mg/cm², 0.01 mg/cm² to 0.075 mg/cm², 0.01 mg/cm² to 0.05 mg/cm², or 0.01 mg/cm² to 0.025 mg/cm². In particular embodiments, the TOC in water is less than an amount in a range from 0.05 mg/cm² to 0.1 mg/cm², 0.05 mg/cm² to 0.09 mg/cm², 0.05 mg/cm² to 0.075 mg/cm², or 0.05 mg/cm² to 0.06 mg/cm² In particular embodiments, the TOC in water is less than an amount in a range from 0.005 mg/cm² to 0.1 mg/cm², 0.005 mg/cm² to 0.095 mg/cm², 0.005 mg/cm² to 0.075 mg/cm², 0.005 mg/cm² to 0.05 mg/cm², 0.005 mg/cm² to 0.025 mg/cm², or 0.005 mg/cm² to 0.01 mg/cm².

The materials used in the oxygen permeable films of the current embodiments may have a defined permeability. The permeability of the oxygen permeable elastomer films is at least 100 cc/m² per day, preferably at least 500 cc/m² per day, preferably at least 1000 cc/m² per day, preferably at least 1500 cc/m² per day, and most preferably at least 2000 cc/m² per day and even more preferably at least 2200 cc/m² per day. The permeability of the oxygen permeable elastomer fluoropolymer composite films is at least 100 cc/m² per day, preferably at least 500 cc/m² per day, preferably at least 1000 cc/m² per day, preferably at least 1500 cc/m² per day, and most preferably at least 2000 cc/m² per day and even more preferably at least 2200 cc/m² per day. Oxygen permeability is measured with a MOCON Ox-tran 2/21H Oxygen Analyzer, following ASTM D3985, at 25° C. In another aspect of film permeablility, normalized units (cc-mm/m²-day) can be used to show a film of any thickness. For example, the converted range for a 5 mil film would be from about 12.7 cc-mm/m²-day to at least about 279 cc-mm/m²-day at a temperature of 25° C. The permeability of the contruct/composite can stay in cc/m² terms as it would be comprised of two layers.

The thickness of outer films 15 and 16 can vary upon application and desired container volume. The thickness of outer films 15 and 16 may be from 1 mil to 30 mils, more particularly from 5 to 10 mils (0.001 of an inch (0.0254 mm)). Container 10 and 11 volumes may range from 2 to 46 in² but are not limited to this range.

Membrane 55 can be attached to outer bag 16 and membranes 50 and 60 can be attached outer film 15 by RF welding, ultrasonic welding, hot bar welding, chemical bonding, adhesive bonding, thermal fusion bonding, solvent welding, laser welding, corona discharge, radiation, extreme heat or melt lamination, etching, plasma treatment, wetting, adhesives, or combinations thereof.

Fluoropolymers are a preferred for use in culture bags because they are biologically, chemically and immunologically inert. Fluoropolymer membranes 50, 55, and 60, each independently, of the current disclosure can comprise FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), PCTFE (polychlorotrifluoroethylene), ETFE (polyethylenetetrafluoroethylene), ECTFE (polyethylenechlorotrifluoroethylene), FFPM/FFKM (perfluoroelastomer), FPM/FKM (chlorotrifluoroethylenevinylidene fluoride), PFPE (perfluoropolyether), MFA (tetrafuoroethylene and perfuoromethyl vinyl-ether copolymer), CTFE/VDF (chlorotrifuoroethylene-vinylidene fluoride copolymer), and TFE/HFP (tetrafuoroethylene-hexafuoropropylene copolymer), or mixtures thereof.

In a preferred embodiment fluoropolymer membranes 50, 55, and 60 are FEP (fluorinated ethylene-propylene).

FEP is a copolymer of hexafluoropropylene and tetrafluoroethylene. It is flexible, extremely resistance to chemical attack, highly transparent, and resistant to sunlight. It is preferred that FEP contains no plasticizers, leachables or extractables that can adversely affect cell cultures.

Fluoropolymer membranes 50, 55, and 60 are semi-permeable that act as barriers to keep the cultured cells within central compartment 20 of container 10 and second compartment 35 of container 11, while permitting media and nutrients to pass. Fluoropolymer membranes 50, 55, and 60 can be manufactured having functional pore size of up to 5 mm in diameter, typically greater than about 100 micron, greater than 500 in diameter, but mostpreferably from about 100 to about 1000 microns in diameter.

The semi-permeable fluoropolymer membranes contain pores that control diffusion by the effective size of the nutrients. Pore size is measure of the pore diameter within a porous material. Pore size that is applicable to cell culture can vary from about 1 to about 30 microns. Pore size in a given material is commonly graded as extra fine, fine, medium, course, and extra course.

The pore size within membranes 50, 55, and 60 allows for movement of media nutrients, metabolites, and cell culture additives through the pores but blocks the cells located within second compartment 35 to pass into first compartment 25 of container 11 and blocks the cells located within central compartment 20 to pass into first and second lateral compartments 30 and 40 of container 10. Pore size can be selected based on cell type cultivation required. For example monocytes have a functional diameter of 12-20 microns, lymphocytes (T, B, and NK cells) have a functional diameter of 7-15 microns, and neutrophils have a functional diameter of 10-12 microns. Not to be limiting, the containers disclosed herein are useful with such biological materials described herein.

Common compounds that can freely diffuse through membranes 50, 55, and 60 comprise glucose (180 Da), glutamine (146 Da), lactic acid/lactate (90 Da), carbon dioxide (44 Da) oxygen (32 Da), ammonia (18 Da), and water (18 Da).

Additionally, the pore size may not be required to be actually smaller than the functional cell diameter of interest where gravity control may help permit adequate function of the culture compartment by preventing cells from diffusing through the membrane.

Porosity is a measure of the pore density of a material, and is a fraction of the volume of pores over the total volume, usually indicated as a percentage between 0 and 100%. Porosity can be measured by employing several porosimetry methods. These methods include direct, optical, computed tomography, imbibition, water evaporation, mercury intrusion, gas expansion, thermoporosimetry, and cryoporometry methods.

The porosity of membranes 50, 55, and 60 in the current embodiments can be from about 10% to about 90%, preferably from about 30% to about 70%, and most preferable from about 40% to about 60%.

The holes in fluoropolymer membranes 50, 55, and 60 can be predrilled by ultraviolet lasers. Laser drilling is a method of micro-machining that relies on controlled ablation. Laser ablation is the process of removing material from a solid (or occasionally liquid) surface by laser beam irradiation. At low laser flux, the material is heated by the absorbed laser energy and evaporates or sublimates. At high laser flux, the material is typically converted to a plasma. Usually, laser ablation refers to removing material with a pulsed laser, but it is possible to ablate material with a continuous wave laser beam if the laser intensity is high enough. Laser ablation is available commercially from companies including MLPC Inc., Kettering Ohio and Resonetics, Nashua N.H. This process is applicable to form holes or openings with diameters as small as 1 micron.

The holes in fluoropolymer membranes 50, 55, and 60 can be predrilled by electron beam drilling (EB). EB drilling is similar to laser drilling in that energy is created and precisely focused on a workpiece to bring about highly localized melting. In the EB process, an electrically heated cathode produces electrons that are accelerated by an electrical field applied between a cathode and anode at a very high voltage. A modulating electrode controls the intensity of the electron beam, which is focused onto the workpiece through an electromagnetic lens to power densities of 100 million watts or more per square centimeter. EB drilling is available commercially from companies including Acceleron Inc., East Granby Conn. and Precision Technologies Inc., Enfield Conn. This process is applicable to form holes or openings as small as 50 microns in diameter.

The holes in fluoropolymer membranes 50, 55, and 60 can also be predrilled by electrical discharge machining (EDM). An EDM microdrilling machine is essentially a sinker or ram-type EDM machine with some interesting modifications that enable it to drill holes as small as 5 microns in diameter.

Additionally, the holes in fluoropolymer membranes 50, 55, and 60 may also be predrilled by mechanical drilling, thermal perforation, or $CO_2$ laser. In a specific embodiment, $CO_2$ lasers are used to drill but ultrafast lasers including femtosecound and picosecond laser can also be used.

In container 10, ports 70 and 80 allow access to central compartment 20, port 90 allow access to first lateral compartment 30, and port 100 allow access to second lateral compartment 40.

In container 11, ports 75 and 85 allow access to first compartment 25 and port 95 allows access to compartment 35.

The location of ports 70, 75, 80, 85, 90, and 100 is not restricted to the current configuration and they may be positioned for convenience of use or manufacture but are connected to their respective compartment.

Ports 70, 75, 80, 85, 90, and 100 may comprise an elastomer, a fluoropolymer, PMP (polymethylpentene), tubes that are attached to container 10 and 11 by a collar sealing process by RF welding, ultrasonic welding, hot bar welding, chemical bonding, adhesive bonding, thermal fusion bonding, solvent welding, laser welding, corona discharge, radiation, extreme heat or melt lamination, etching, plasma treatment, wetting, adhesives, or combinations thereof. Preferred methods of welding include thermal, laser, and hot bar welding. Generally, the port material would be the same as the inside layer of the container 10.

The elastomer of ports 70, 75, 80, 85, 90, and 100 can be natural polyisopene rubber (NR), synthetic polyisoprene rubber (IR), polybutadiene rubber (BR), chloropene rubber (CR), butyl rubber (IIR), halogenated butyl rubbers (CIIR, BIIR), styrene-butadiene rubber (SBR), nitrile rubber (NBR) and hydrogenated nitrile rubber (HNBR), ethylene propylene rubber (EPM), ethylene propylene diene rubber (EPDM), epichlorohydrin rubber (ECO), polyacrylic rubber (ACM, ABR), silicone rubber (SI, Q, VMQ), fluorosilicone rubber (FSR, FVMQ), fluoroelastomers (FKM, FEPM), perfluoroelastomers (FFKM), polyether block amides (PEBA), chlorosulfonated polyethylene (CSM), ethylene-vinyl acetate (EVA), or mixtures thereof.

The fluoropolymer of ports 70, 75, 80, 85, 90, and 100 can be FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), PCTFE (polychlorotrifluoroethylene), ETFE (polyethylenetetrafluoroethylene), ECTFE (polyethylenechlorotrifluoroethylene), FFPM/FFKM (perfluoroelastomer), FPM/FKM (chlorotrifluoroethylenevinylidene fluoride), PFPE (perfluoropolyether), MFA (tetrafuoroethylene and perfuoromethyl vinyl-ether copolymer), CTFE/VDF (chlorotrifuoroethylene-vinylidene fluoride copolymer), and TFE/HFP (tetrafluoroethylene-hexafuoropropylene copolymer), or mixtures thereof.

In a preferred embodiment the tubes are FEP (fluorinated ethylene-propylene).

Isolated cells, DNA fragments, and enzymes are introduced to container 10 through port 70 into central compartment 20. Harvested cells are removed from central compartment 20 of container 10 through port 80.

Isolated cells, DNA fragments, or enzymes are introduced and removed from second compartment 35 of container 11 through port 95.

Fresh media can be introduced through port 90 to first lateral compartment 30 of container 10. The media is saturated in oxygen, cytokines, and essential nutrients for cell culture which all can freely permeate through first fluoropolymer membrane 50.

Fresh media can be introduced through port 75 to first compartment 25 of container 11 and removed through port 85. Essential nutrients can freely permeate through fluoropolymer membrane 55.

Waste media is removed through port 100 from second lateral compartment 40. The waste media is saturated in carbon dioxide, organic acids, and other cell waste material.

In another embodiment, filling also could happen completely through one port but the perfusion would be from one port to another with the components of the media being able to freely diffuse as the media is in both compartments with no air gap in between.

In yet another embodiment, containers such as bags that include or do not include membranes can also contain a perfusion tube or tubes that may be used with filters to allow perfusion of media in and out without cell loss. This system would find use when a) the membrane in the center of the bag is not used and the filter containing perfusion tube or tubes are used to prevent cell loss and when b) the membrane is still used but the filter containing perfusion tube or tubes are added for additional prevention of cell loss.

Containers 10 and 11 can provide a static and closed environment for cell cultivation.

Containers 10 and 11 can also permit the input of fresh media and the removal of waste media while preventing the loss or death of cultured cells. Input of fresh media and the removal of waste media can be perfused continuously or repeated periodically. A disposable sensor to measure pH/DO can also be included in the bags to monitor cell culture conditions.

Perfusion ranges applicable herein are from about 0.05 mL/min to about 20 mL/min (assuming a bag volume of 290 mL). A slow perfusion rate is for when there is no recycle and/or the cells have low consumption/low waste production and is generally limited by pump equipment. A high perfusion rate is for when there is a recycle and/or the cells have high consumption/high waste production. This is limited by effect of the flow on the cells in lower compartment. In another embodiment, the perfusion rate is equated as from 0.01 to 4.2 volumes/hr. (0.25-100 volumes/day) so that it can be applied to a wide variety of bag volumes. Oxygen transmission rates (OTR) of the embodiments disclosed herein range from about 1,000 to about 200,000 $cm^3/m^2$/day.

The diameter of the holes in fluoropolymer membranes 50, 55, and 60 is sufficient to retain the cells within their respective compartment, thereby permitting cell proliferation and concentration. The following paragraphs enumerated consecutively from 1 through 43 provide for various aspects of the present invention.

In one embodiment, in a first paragraph (1), the present invention provides a container comprising a gas permeable outer film comprising a polymer having a total organic carbon (TOC) in water of less than 0.1 $mg/cm^2$, and a membrane separating a first compartment from a second compartment, wherein the membrane comprises a polymer having a TOC in water of less than 0.1 $mg/cm^2$, and wherein the gas permeable outer film and the membrane define walls of the first and second compartments.

2. The container according to paragraph 1, wherein the gas permeable outer film is a silicone and the membrane is a fluoropolymer.

3. The container according to paragraph 1, wherein the gas permeable outer film and the membrane are each individually an elastomer, a fluoropolymer, PMP (polymethylpentene), or combinations thereof.

4. The container according to paragraph 2, wherein the fluoropolymer membrane is FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), PCTFE (polychlorotrifluoroethylene), ETFE (polyethylenetetrafluoroethylene), ECTFE (polyethylenechlorotrifluoroethylene), FFPM/FFKM (perfluoroelastomer), FPM/FKM (chlorotrifluoroethylenevinylidene fluoride), PFPE (perfluoropolyether), MFA (tetrafuoroethylene and perfuoromethyl vinyl-ether copolymer), CTFE/VDF (chlorotrifuoroethylene-vinylidene fluoride copolymer), and TFE/HFP (tetrafuoroethylene-hexafuoropropylene copolymer), or mixtures thereof.

5. The container according to paragraph 4, wherein the fluoropolymer membrane comprises holes formed by ultraviolet laser drilling, electron beam drilling, electrical discharge machining, mechanical drilling, thermal perforation, or $CO_2$ laser.

6. The container according to paragraph 5, wherein the holes are up to 5 mm in diameter.

7. The container according to paragraph 5, wherein the holes are greater than 100 microns, greater than 500 microns, and up to 5 mm in diameter.

8. The container according to paragraph 5, wherein the holes are from about 50 microns to about 100 microns in diameter.

9. The container according to paragraph 5 through 8, wherein the porosity is from about 10% to about 90%.

10. The container according to paragraph 5 through 9, wherein the porosity is from about 20% to about 70%.

11. The container according to paragraph 5 through 10, wherein the porosity is from about 30% to about 50%.

12. The container according to paragraph 1, wherein the fluoropolymer membrane is attached to the container by chemical bonding, adhesive bonding, thermal fusion bonding, solvent bonding, welding, surface treatment, UV welding, RF welding, laser welding, hot bar welding, or combinations thereof.

13. The container according to paragraph 1, wherein the container comprises at least two ports, wherein a first port is attached to the first compartment, a second port is attached to the second compartment.

14. The container according to paragraph 13, wherein the ports comprise an elastomer, a fluoropolymer, PMP (polymethylpentene), or combinations thereof.

15. The container according to paragraph 14, wherein the ports are attached to the container by chemical bonding, adhesive bonding, thermal fusion bonding, solvent bonding, welding, surface treatment, UV welding, RF welding, laser welding, hot bar welding, or combinations thereof.

16. A container comprising a gas permeable outer film comprising a polymer having a total organic carbon (TOC) in water of less than 0.1 $mg/cm^2$, a first membrane separating a central compartment from a first lateral compartment, and a second membrane separating the central compartment from a second lateral compartment, wherein the central compartment is between the first and second lateral compartments, wherein the first and second membranes both comprise a polymer having a TOC in water of less than 0.1 $mg/cm^2$, and wherein the gas permeable outer film and the first and second membranes define walls of the first lateral, second lateral, and central compartments.

17. The container according to paragraph 16, wherein the gas permeable outer film is a silicone and the first and second membranes are fluoropolymers.

18. The container according to paragraph 16, wherein the gas permeable outer film and the first and second membranes are each individuarlly an elastomer, a fluoropolymer, PMP (polymethylpentene), or combinations thereof.

19. The container according to paragraph 17, wherein the first and second fluoropolymer membranes are FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), PCTFE (polychlorotrifluoroethylene), ETFE (polyethylenetetrafluoroethylene), ECTFE (polyethylenechlorotrifluoroethylene), FFPM/FFKM (perfluoroelastomer), FPM/FKM (chlorotrifluoroethylenevinylidene fluoride), PFPE (perfluoropolyether), MFA (tetrafuoroethylene and perfuoromethyl vinyl-ether copolymer), CTFE/VDF (chlorotrifuoroethylene-vinylidene fluoride copolymer), and TFE/HFP (tetrafuoroethylene-hexafuoropropylene copolymer), or mixtures thereof.

20. The container according to paragraph 19, wherein the first and second fluoropolymer membranes comprise holes formed by ultraviolet laser drilling, electron beam drilling, electrical discharge machining, mechanical drilling, thermal perforation, or $CO_2$ laser.

21. The container according to paragraph 20, wherein the holes are up to 5 mm in diameter.

22. The container according to paragraph 20, wherein the holes are greater than 100 microns, greater than 500 microns, and up to 5 mm in diameter.

23. The container according to paragraph 20, wherein the holes are from about 50 microns to about 100 microns in diameter.

24. The container according to paragraph 20 through 23, wherein the porosity is from about 10% to about 90%.

25. The container according to paragraph 20 through 24, wherein the porosity is from about 20% to about 70%.

26. The container according to paragraph 20 through 25, wherein the porosity from about 30% to about 50%.

27. The container according to paragraph 16, wherein the fluoropolymer membranes are attached to the container by chemical bonding, adhesive bonding, thermal fusion bonding, solvent bonding, welding, surface treatment, UV welding, RF welding, laser welding, hot bar welding, or combinations thereof.

28. The container according to paragraph 16, wherein the container comprises at least two ports, wherein a first port is attached to the first lateral compartment, a second port is attached to the second lateral compartment, and a third port is attached to the central compartment.

29. The container according to paragraph 28, wherein the ports comprise an elastomer, a fluoropolymer, PMP (polymethylpentene), or combinations thereof.

30. The container according to paragraph 29, wherein the ports are attached to the container by chemical bonding, adhesive bonding, thermal fusion bonding, solvent bonding, welding, surface treatment, or combinations thereof.

31. A method to cultivate cells in a container comprising a gas permeable outer film comprising a polymer having a total organic carbon (TOC) in water of less than 0.1 mg/cm$^2$, a membrane separating a first compartment from a second compartment, wherein the membrane comprises a polymer having a TOC in water of less than 0.1 mg/cm$^2$, and wherein the gas permeable outer film and the membrane define walls of the first and second compartments, and at least two ports, wherein the first port is attached to the first compartment, and the second port is attached to the second compartment comprising the steps of: a) adding media to the first compartment through the first port; b) adding media and cells to the second compartment through the second port; and c) removing waste media from the first compartment through the first port or a third port, wherein the media permeates from between the first and second compartments through the membrane.

32. The method according to paragraph 31, further comprising the step of incubating the container.

33. The method according to paragraph 32, wherein the cell incubation is static agitated, rocked, or stirred.

34. The method according to paragraph 32, further comprising the step of flowing media through the container.

35. The method according to paragraph 32, further comprising the step of harvesting cells from the first compartment through the first port.

36. The method according to paragraph 31, wherein the diameter of the holes in the fluoropolymer membrane are sufficient to retain the cells within the first compartment.

37. A method to cultivate cells in a container comprising a gas permeable outer film comprising a polymer having a total organic carbon (TOC) in water of less than 0.1 mg/cm$^2$, a first membrane separating a central compartment from a first lateral compartment, a second membrane separating the central compartment from a second lateral compartment, wherein the central compartment is between the first and second lateral compartments, wherein the first and second membranes both comprise a polymer having a TOC in water of less than 0.1 mg/cm$^2$, and wherein the gas permeable outer film and the first and second membranes define walls of the first lateral, second lateral, and central compartments, and at least three ports, wherein the first port is attached to the first lateral compartment, the second port is attached to the second lateral compartment, and the third port is attached to the central compartment comprising the steps of: a) adding cells to the central compartment through the third port; b) adding media to the first lateral compartment through the first port; and c) removing waste media from the second lateral compartment through the second port, wherein the media permeates from the first lateral compartment to the central compartment through the first membrane and the waste media permeates from the central compartment to second lateral compartment through the second membrane.

38. The method according to paragraph 37, further comprising the step of incubating the container.

39. The method according to paragraph 38, wherein the cell incubation is static, agitated, rocked, or stirred.

40. The method according to paragraph 38, further comprising the step of flowing media through the container.

41. The method according to paragraph 38, further comprising the step of harvesting cells from the central compartment through the third port.

42. The method according to paragraph 37, wherein the diameter of the holes in the membrane are sufficient to retain the cells within the central compartment.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Tested Samples

TABLE 1

TOC data

| Material | Form | Extraction Conditions | TOC (TOC-Blank) |
|---|---|---|---|
| PMP Film | Film | 70° C., 24 hours, 3 cm$^2$/mL | 0.07 ppm (0.00001 mg/cm$^2$) |
| Primed Thermoset Silicone/1 mil FEP Laminate | Bag with Laminate as bottom sheet | 70° C., 24 hours, 3 cm$^2$/mL | 0.02 ppm (0.00001 mg/cm$^2$) |
| Unprimed Thermoset Silicone/1 mil FEP Laminate | Bag with Laminate as bottom sheet | 70° C., 24 hours, 3 cm$^2$/mL | 0.01 ppm (0.000003 mg/cm$^2$) |
| PMP/1 mil FEP Laminate | Bag with Laminate in cut-out bag form (i.e. portion of bottom sheet) | 70° C., 24 hours, 3 cm$^2$/mL | 0.01 ppm (0.000003 mg/cm$^2$) |
| Thermoplastic Silicone/1 mil FEP Laminate (with liner) | Bag with Laminate in cut-out bag form (i.e. portion of bottom sheet) | 70° C., 24 hours, 3 cm$^2$/mL | 0.36 ppm (0.0001 mg/cm$^2$) |
| Thermoplastic Silicone/1 mil FEP Laminate (without liner) | Bag with Laminate in cut-out bag form (i.e. portion of bottom sheet) | 70° C., 24 hours, 3 cm$^2$/mL | 3.59 ppm (0.001 mg/cm$^2$) |
| FEP "Incumbent" | 2PF-0290 FEP Bag | 70° C., 24 hours, 3 cm$^2$/mL | 0.30 ppm (0.0001 mg/cm$^2$) | ppm = mg/L

Example 2

Dissolved Oxygen Experiments

Incumbent FEP bag made from 5 mil FEP on top and bottom and a prototype bag made from 5 mil FEP on top and thermoplastic silicone/FEP on the bottom were filled to 300 mL and 190 mL respectively with tap water. These volumes correlate to a 1 cm thickness of water in the bag when it is lying flat, a recommendation that is well-known in industry. A port was cut out of each bag in order to feed in a nitrogen line to purge the water in the bag to a level below saturation. Dissolved oxygen (DO) levels were monitored using the PreSens probe affixed to the outside of the bag and aligned with the sensor dot on the inside of the bag. When the DO levels in the water reached a reasonably low value (~6-8%), the nitrogen line was removed from the bag and the port opening was clamped shut. The bag and rack were returned to a horizontal resting position for the remainder of the experiment. The PreSens probe was programmed to take DO measurements at designated time points in order to measure the ingress of oxygen as a function of time. It was assumed that the only path for oxygen ingress was through the walls of the bags.

Figure 6:
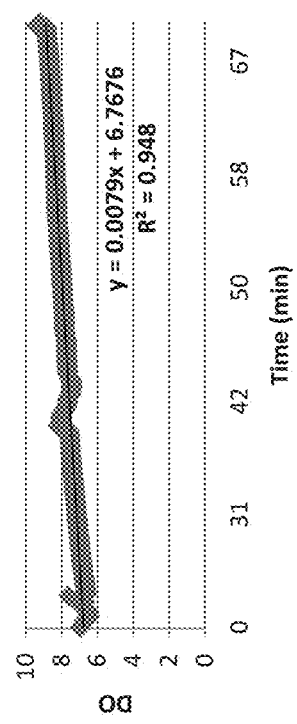
FIG. 6 shows a graphical representation of the initial ingress of oxygen into incumbent FEP bag.
Figure 7:
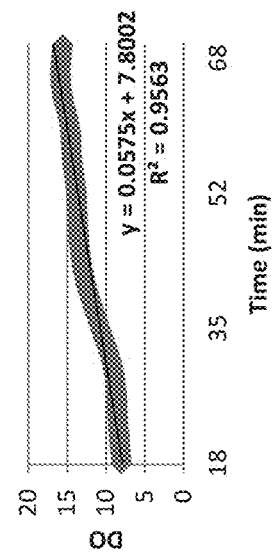
FIG. 7 shows a graphical representation of the initial ingress of oxygen in prototype bag with gas permeable laminate.
Figure 8:
FIG. 8 shows a graphical representation of the approach to equilibrium in prototype bag made with gas permeable laminate.

Results:

Measurements from the PreSens system were downloaded and plotted in Excel for both bags (FIGS. 6, 7, and 8). The data was studied and observations were made to bracket the data. For instance, for the prototype bag, the beginning measurements were excluded because the bag was moved and manipulated in order to remove an air bubble from above the sensor. Also, because a longer measurement was taken for the prototype bag, the data was split into two linear sections, "Initial Ingress" and "Approach to Equilibrium". Due to this, the best comparison to make with the current data available is between FIG. 6 and FIG. 7 which demonstrate the initial ingress of oxygen into each of the bags as a function of time when starting at similar DO levels (~6-8%) for a similar amount of time (~68-70 min). Looking at FIG. 6 and FIG. 7, the comparison of slopes can be made to understand the difference in rate of ingress between the incumbent and prototype bags. The incumbent bag as a rate of 0.008% DO/min while the prototype bag has a rate of 0.06% DO/min, a difference of over 7x. This alludes to the positive impact of the more permeable material on the ingress of oxygen.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A container comprising:
   a gas permeable outer film defining an outside of the container, the gas permeable outer film comprising a polymer having a total organic carbon (TOC) in water of less than 0.1 mg/cm$^2$; and a fluoropolymer membrane separating a first compartment from a second compartment, wherein the membrane comprises a polymer having a TOC in water of less than 0.1 mg/cm$^2$, and wherein the gas permeable outer film and the fluoropolymer membrane define walls of the first and second compartments, wherein the fluoropolymer membrane is formed from FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), PCTFE (polychlorotrifluoroethylene), ETFE (polyethylenetetrafluoroethylene), ECTFE (polyethylenechlorotrifluoroethylene), FFPM/FFKM (perfluoroelastomer), FPM/FKM (chlorotrifluoroethylenevinylidene fluoride), PFPE (perfluoropolyether), MFA (tetrafuoroethylene and perfuoromethyl vinyl-ether copolymer), CTFE/VDF (chlorotrifuoroethylene-vinylidene fluoride copolymer), and TFE/HFP (tetrafuoroethylene-hexafuoropropylene copolymer), or a mixture of two or more thereof, and wherein the fluoropolymer membrane comprises holes formed by ultraviolet laser drilling, electron beam drilling, electrical discharge machining, mechanical drilling, thermal perforation, or CO$_2$ laser.

2. The container of claim 1, wherein the gas permeable outer film is a silicone.

3. The container of claim 1, wherein the gas permeable outer film is an elastomer, a fluoropolymer, PMP (polymethylpentene), or combinations thereof.

4. The container of claim 1, wherein the fluoropolymer membrane is FEP (fluorinated ethylene-propylene).

5. The container of claim 1, wherein the holes are up to 5 mm in diameter.

6. The container of claim 1, wherein the porosity is from about 30% to about 50%.

7. A container comprising:
    a gas permeable outer film defining an outside of the container, the gas permeable outer film comprising a polymer having a total organic carbon (TOC) in water of less than 0.1 mg/cm$^2$;
    a first fluoropolymer membrane separating a central compartment from a first lateral compartment; and
    a second fluoropolymer membrane separating the central compartment from a second lateral compartment, wherein the central compartment is between the first and second lateral compartments, wherein the first and second membranes both comprise a polymer having a TOC in water of less than 0.1 mg/cm$^2$, and wherein the one or more gas permeable outer films and the first and second membranes define walls of the first lateral, second lateral, and central compartments, wherein each of the first and second fluoropolymer membranes is formed from FEP (fluorinated ethylene-propylene), TFE (tetrafluoroethylene), PFA (perfluoroalkoxy), PVF (polyvinylfluoride), PVDF (polyvinylidene fluoride), PTFE (polytetrafluoroethylene), PCTFE (polychlorotrifluoroethylene), ETFE (polyethylenetetrafluoroethylene), ECTFE (polyethylenechlorotrifluoroethylene), FFPM/FFKM (perfluoroelastomer), FPM/FKM (chlorotrifluoroethylenevinylidene fluoride), PFPE (perfluoropolyether), MFA (tetrafuoroethylene and perfuoromethyl vinyl-ether copolymer), CTFE/VDF (chlorotrifuoroethylene-vinylidene fluoride copolymer), and TFE/HFP (tetrafuoroethylene-hexafuoropropylene copolymer), or a mixture of two or more thereof, and wherein the each of the first and second fluoropolymer membrane comprises holes formed by ultraviolet laser drilling, electron beam drilling, electrical discharge machining, mechanical drilling, thermal perforation, or CO$_2$ laser.

8. The container of claim 7, wherein the gas permeable outer film is a silicone.

9. The container of claim 7, wherein the gas permeable outer film is an elastomer, a fluoropolymer, PMP (polymethylpentene), or combinations thereof.

10. The container of claim 7, wherein the first and second fluoropolymer membranes are FEP (fluorinated ethylene-propylene).

11. The container of claim 7, wherein the holes are up to 5 mm in diameter.

12. The container of claim 11, wherein the porosity is from about 10% to about 90%.

13. A method to cultivate cells in a container according to claim 1, the container further comprising:
    at least two ports, wherein the first port is attached to the first compartment, and the second port is attached to the second compartment,
    the method comprising the steps of:
    a) adding media to the first compartment through the first port;
    b) adding media and cells to the second compartment through the second port; and
    c) removing waste media from the first compartment through the first port or a third port, wherein the media permeates from between the first and second compartments through the membrane.

14. The method of claim 13, further comprising the step of incubating the contents of the container.

15. The method of claim 14, wherein the container is static agitated, rocked, or stirred during the incubation.

16. The method of claim 14, further comprising the step of flowing media through the container.

17. The method of claim 14, further comprising the step of harvesting cells from the first compartment through the first port.

18. The method of claim 13, wherein the diameter of the holes in the membrane are sufficient to retain the cells within the first compartment.

19. The container of claim 1, wherein the holes are from about 50 microns to about 100 microns in diameter.

20. The container of claim 1, wherein the TOC in water of the fluoropolymer membrane is less than 0.01 mg/cm$^2$.

21. The container of claim 20, wherein the TOC in water of each of the one or more gas permeable outer films is less than 0.01 mg/cm$^2$.

22. The container of claim 1, wherein the gas permeable outer film is a laminate of a fluoropolymer and a material selected from PMP and thermoplastic silicone.

* * * * *